US009022628B2

(12) United States Patent
Krupa et al.

(10) Patent No.: US 9,022,628 B2
(45) Date of Patent: May 5, 2015

(54) COMPACT, HIGH EFFICIENCY, HIGH POWER SOLID STATE LIGHT SOURCE USING A SINGLE SOLID STATE LIGHT-EMITTING DEVICE

(75) Inventors: Robert J. Krupa, Leominster, MA (US); Peter G. Lorenz, Massapequa, NY (US); Thomas V. Root, Beverly, MA (US)

(73) Assignee: Optim, Inc., Sturbridge, MA (US)

( * ) Notice: Subject to any disclaimer, the term of this patent is extended or adjusted under 35 U.S.C. 154(b) by 0 days.

(21) Appl. No.: 12/252,845

(22) Filed: Oct. 16, 2008

(65) Prior Publication Data
US 2009/0040783 A1 Feb. 12, 2009

Related U.S. Application Data

(63) Continuation of application No. 11/636,941, filed on Dec. 11, 2006, now Pat. No. 8,033,704, which is a continuation of application No. 10/810,504, filed on Mar. 26, 2004, now Pat. No. 7,229,201.

(60) Provisional application No. 60/457,672, filed on Mar. 26, 2003.

(51) Int. Cl.
*F21V 8/00* (2006.01)
*A61B 1/06* (2006.01)
(52) U.S. Cl.
CPC ............ *G02B 6/0006* (2013.01); *A61B 1/0684* (2013.01)
(58) Field of Classification Search
USPC ............... 362/572–574, 119, 249.01, 249.02, 362/231, 516, 517, 551, 554–556, 612, 613, 362/615, 621; 257/81, 79, 82, 88, 94, 98, 257/99; 385/119, 28, 31–34, 92, 115–117, 385/120, 121, 146, 901
See application file for complete search history.

(56) References Cited

U.S. PATENT DOCUMENTS

| 2,235,979 A | 3/1941 | Brown |
| 3,111,230 A | 11/1963 | Pesenti |
| 3,299,731 A | 1/1967 | Russell, Jr. |
| 3,365,975 A | 1/1968 | Hathaway |
| 3,394,611 A | 7/1968 | Beurrier |
| 3,605,730 A | 9/1971 | Hotchkiss |

(Continued)

FOREIGN PATENT DOCUMENTS

| DE | 202 11713 | 12/2002 |
| EP | 1396754 | 3/2004 |

(Continued)

OTHER PUBLICATIONS

Microsemi product brochure of UPW3LEDxx, published Jul. 25, 2003.
Photograph of Microsemi's UPW3LEDxx, Publication Jul. 25, 2003.
International Search Report for PCT Application No. PCT/US2009/032050 mailed on Jul. 10, 2009 (3pg).

(Continued)

*Primary Examiner* — Hargobind S Sawhney
(74) *Attorney, Agent, or Firm* — Burns & Levinson LLP

(57) ABSTRACT

A compact, high-efficiency, high-power, solid state light source, comprising a high-power solid state light-emitting device, a light guide having a proximal light-receiving end proximate the light-emitting device and a distal light-transmitting end spaced farther from the light-emitting device, and a mechanical light guide fixing device coupled to the light guide near its proximal end, to hold the proximal end of the light guide in position near the light-emitting device.

23 Claims, 4 Drawing Sheets

(56) References Cited

U.S. PATENT DOCUMENTS

| | | | |
|---|---|---|---|
| 3,756,688 A | 9/1973 | Hudson et al. | |
| 3,832,028 A | 8/1974 | Kapron | |
| 3,938,402 A | 2/1976 | Citrin | |
| 3,963,438 A | 6/1976 | Banez | |
| 3,986,498 A | 10/1976 | Lewis | |
| 4,101,197 A | 7/1978 | Kent et al. | |
| 4,212,021 A * | 7/1980 | Ono et al. | 257/94 |
| 4,241,978 A * | 12/1980 | Dubois et al. | 385/31 |
| 4,281,891 A | 8/1981 | Shinohara et al. | |
| 4,385,344 A | 5/1983 | Gonser | |
| 4,449,518 A | 5/1984 | Konomura et al. | |
| 4,534,208 A | 8/1985 | Macin et al. | |
| 4,617,915 A | 10/1986 | Arakawa | |
| 4,639,845 A | 1/1987 | Persson et al. | |
| 4,739,128 A | 4/1988 | Grisham | |
| 4,763,100 A | 8/1988 | Wood | |
| 4,763,975 A | 8/1988 | Scifres et al. | |
| 4,836,782 A | 6/1989 | Gonser | |
| 4,850,716 A | 7/1989 | Baker et al. | |
| 4,862,872 A | 9/1989 | Yabe et al. | |
| 4,907,133 A | 3/1990 | Nath | |
| 4,919,113 A | 4/1990 | Sakamoto et al. | |
| 4,974,607 A | 12/1990 | Miwa | |
| 4,998,926 A | 3/1991 | Alchas | |
| 5,050,449 A | 9/1991 | Falcou et al. | |
| 5,065,011 A | 11/1991 | Fujihara et al. | |
| 5,098,292 A | 3/1992 | Lazarof | |
| 5,107,537 A | 4/1992 | Schricks et al. | |
| D330,020 S | 10/1992 | Jung | |
| D333,601 S | 3/1993 | Wingert | |
| 5,217,003 A | 6/1993 | Wilk | |
| 5,238,025 A | 8/1993 | Preston | |
| 5,271,079 A * | 12/1993 | Levinson | 385/46 |
| 5,290,169 A | 3/1994 | Friedman et al. | |
| 5,290,279 A | 3/1994 | Bonati et al. | |
| 5,359,993 A | 11/1994 | Slater et al. | |
| 5,368,015 A | 11/1994 | Wilk | |
| 5,373,317 A | 12/1994 | Salvati et al. | |
| 5,408,991 A | 4/1995 | Iida et al. | |
| D358,471 S | 5/1995 | Cope et al. | |
| 5,420,768 A | 5/1995 | Kennedy | |
| 5,434,941 A | 7/1995 | Bechtel et al. | |
| 5,497,847 A | 3/1996 | Ota et al. | |
| 5,535,141 A | 7/1996 | Lüssi | |
| 5,537,503 A | 7/1996 | Tojo et al. | |
| 5,586,207 A | 12/1996 | Goodwin | |
| 5,609,561 A | 3/1997 | Uehara et al. | |
| 5,631,987 A | 5/1997 | Lasky et al. | |
| 5,634,711 A | 6/1997 | Kennedy et al. | |
| 5,655,411 A | 8/1997 | Avitan et al. | |
| 5,680,492 A | 10/1997 | Hopler et al. | |
| 5,687,270 A | 11/1997 | Takizawa | |
| 5,718,664 A | 2/1998 | Peck et al. | |
| 5,723,868 A * | 3/1998 | Hammond et al. | 250/553 |
| 5,732,401 A | 3/1998 | Conway | |
| 5,761,364 A | 6/1998 | Knapp et al. | |
| 5,803,729 A | 9/1998 | Tsimerman | |
| 5,830,121 A | 11/1998 | Enomoto et al. | |
| 5,846,183 A | 12/1998 | Chilcoat | |
| 5,888,194 A | 3/1999 | Utsumi et al. | |
| 5,895,350 A | 4/1999 | Hori | |
| 5,920,054 A | 7/1999 | Uber, III | |
| 5,975,895 A | 11/1999 | Sullivan | |
| 5,984,875 A | 11/1999 | Brune | |
| 6,059,718 A | 5/2000 | Taniguchi et al. | |
| 6,092,722 A | 7/2000 | Heinrichs et al. | |
| 6,092,935 A | 7/2000 | Althaus et al. | |
| 6,159,005 A | 12/2000 | Herold et al. | |
| 6,193,510 B1 | 2/2001 | Tsimerman | |
| 6,239,496 B1 * | 5/2001 | Asada | 257/777 |
| 6,240,312 B1 | 5/2001 | Alfano et al. | |
| 6,260,994 B1 | 7/2001 | Matsumoto et al. | |
| 6,318,887 B1 | 11/2001 | Matsumoto | |
| 6,331,156 B1 | 12/2001 | Haefele et al. | |
| 6,366,206 B1 | 4/2002 | Ishikawa et al. | |
| 6,436,032 B1 | 8/2002 | Eto et al. | |
| 6,436,035 B1 | 8/2002 | Toth et al. | |
| 6,438,302 B1 | 8/2002 | Utsui et al. | |
| 6,452,624 B1 | 9/2002 | Aloy | |
| 6,461,295 B2 | 10/2002 | Takada | |
| 6,485,684 B1 | 11/2002 | Mapson et al. | |
| D466,773 S | 12/2002 | Lin | |
| 6,572,280 B2 | 6/2003 | Hurt et al. | |
| 6,653,765 B1 * | 11/2003 | Levinson et al. | 313/112 |
| 6,679,835 B2 | 1/2004 | Moriyama | |
| 6,692,251 B1 | 2/2004 | Logan et al. | |
| 6,692,431 B2 | 2/2004 | Kazakevich | |
| 6,712,756 B1 | 3/2004 | Kura et al. | |
| 6,712,760 B2 | 3/2004 | Sano et al. | |
| 6,726,620 B2 | 4/2004 | Shibata et al. | |
| 6,730,731 B2 | 5/2004 | Tobita et al. | |
| 6,776,537 B2 * | 8/2004 | Toyama | 385/93 |
| 6,785,433 B2 | 8/2004 | Tiefenthaler | |
| 6,793,622 B2 | 9/2004 | Konomura et al. | |
| 6,812,066 B2 * | 11/2004 | Taniguchi et al. | 438/121 |
| 6,814,932 B2 | 11/2004 | Hlebovy et al. | |
| 6,832,849 B2 | 12/2004 | Yoneda et al. | |
| 6,884,392 B2 | 4/2005 | Malkin et al. | |
| 6,885,106 B1 * | 4/2005 | Damberg et al. | 257/777 |
| 6,918,693 B2 | 7/2005 | Ota et al. | |
| 6,921,920 B2 * | 7/2005 | Kazakevich | 257/81 |
| 6,932,599 B1 | 8/2005 | Hartung | |
| 6,950,573 B2 | 9/2005 | Ota et al. | |
| 7,063,450 B2 | 6/2006 | Ehara et al. | |
| 7,198,397 B2 | 4/2007 | Bennett et al. | |
| 7,252,408 B2 | 8/2007 | Mazzochette et al. | |
| 7,645,056 B1 | 1/2010 | Mills et al. | |
| 2001/0033807 A1 | 10/2001 | Lin et al. | |
| 2001/0056224 A1 | 12/2001 | Renner et al. | |
| 2002/0013510 A1 | 1/2002 | Moriyama | |
| 2002/0120181 A1 | 8/2002 | Irion | |
| 2002/0188173 A1 | 12/2002 | Kobayashi | |
| 2003/0086270 A1 | 5/2003 | Baillie-Hamilton | |
| 2003/0109837 A1 | 6/2003 | McBride-Sakal | |
| 2003/0141507 A1 | 7/2003 | Krames et al. | |
| 2003/0156430 A1 | 8/2003 | Ota et al. | |
| 2003/0201462 A1 | 10/2003 | Pommer et al. | |
| 2003/0231843 A1 | 12/2003 | Columbo et al. | |
| 2003/0235800 A1 | 12/2003 | Qadar | |
| 2004/0004846 A1 | 1/2004 | Steen et al. | |
| 2004/0024290 A1 | 2/2004 | Root et al. | |
| 2004/0041031 A1 | 3/2004 | Root et al. | |
| 2004/0049172 A1 | 3/2004 | Root et al. | |
| 2004/0052485 A1 | 3/2004 | Van Eijkelenborg et al. | |
| 2004/0052679 A1 | 3/2004 | Root et al. | |
| 2004/0059191 A1 | 3/2004 | Krupa et al. | |
| 2004/0091219 A1 | 5/2004 | Christensen et al. | |
| 2004/0225190 A1 | 11/2004 | Kimoto et al. | |
| 2004/0246744 A1 | 12/2004 | Krupa et al. | |
| 2005/0075539 A1 | 4/2005 | Schulz et al. | |
| 2005/0265653 A1 | 12/2005 | Cai et al. | |
| 2006/0158896 A1 | 7/2006 | Krupa et al. | |
| 2007/0086205 A1 | 4/2007 | Krupa et al. | |
| 2007/0274096 A1 | 11/2007 | Chew et al. | |
| 2008/0114207 A1 | 5/2008 | Krupa et al. | |
| 2009/0034286 A1 | 2/2009 | Krupa et al. | |
| 2009/0122573 A1 | 5/2009 | Krupa et al. | |
| 2009/0185392 A1 | 7/2009 | Krupa et al. | |
| 2009/0190371 A1 | 7/2009 | Root et al. | |

FOREIGN PATENT DOCUMENTS

| | | |
|---|---|---|
| GB | 1409793 | 10/1975 |
| JP | 5264871 | 10/1993 |
| JP | 5313045 | 11/1993 |
| JP | 8-317897 | 12/1996 |
| JP | 2002368283 | 12/2002 |
| JP | 2003-135367 | 5/2003 |
| JP | 2004-129720 | 4/2004 |

(56) References Cited

FOREIGN PATENT DOCUMENTS

| WO | WO 99/16136 | 4/1999 |
|---|---|---|
| WO | WO 01/95228 | 12/2001 |
| WO | WO 02/17171 | 2/2002 |
| WO | WO 02/071930 | 9/2002 |
| WO | 2005/103562 | 11/2005 |
| WO | WO 2006/034171 | 3/2006 |
| WO | WO 2006/066022 | 6/2006 |

OTHER PUBLICATIONS

International Search Report for PCT Application No. PCT/US2005/033435 mailed on Jan. 27, 2006 (2 pgs).
International Search Report for PCT Application No. PCT/US2006/048427 mailed on Apr. 27, 2007 (2 pgs).
The International Search Report PCT Application No. PCT/US2010/021567, mailed on Apr. 16, 2010 (2 pages).
Co-Pending U.S. Appl. No. 11/972,489, filed Jan. 10, 2008.

* cited by examiner

COMPACT, HIGH EFFICIENCY, HIGH POWER SOLID STATE LIGHT SOURCE USING A SINGLE SOLID STATE LIGHT-EMITTING DEVICE

CROSS REFERENCE TO RELATED APPLICATION

This application is a continuation application of U.S. Ser. No. 11/636,941, filed Dec. 11, 2006, which is a continuation of U.S. Ser. No. 10/810,504, filed on Mar. 26, 2004, which claims priority of Provisional application Ser. No. 60/457,672, filed on Mar. 26, 2003. The disclosure of each of the applications referenced herein are incorporated by reference in their entirety.

FIELD OF THE INVENTION

This invention relates to a remote illumination device using a high-power LED and a fiber optic light guide.

BACKGROUND OF THE INVENTION

Light sources for endoscopic use are generally of two types: incandescent filament lamps and arc lamps. Incandescent lamps produce light by passing current through a tungsten filament, causing it to radiate light in proportion to its blackbody color temperature. The hotter the filament, the higher its color temperature and the more nearly it approaches daylight with a color temperature of approximately 5500K. Tungsten filament lamps range in color temperature from approximately 2400-3400K. Because of the low color temperature, objects illuminated by a tungsten filament light source appear slightly yellow due to the low output of blue light from these sources. Arc lamps produce light by creating a plasma between two electrodes within the sealed bulb. White light from these lamps can be produced by choosing the appropriate fill gas (usually Xe) and pressure (usually several atmospheres). Color temperature of common arc lamps is approximately 4000-6000K. Both types of lamps, filament and arc, are very inefficient in converting electrical power to light, and consequently produce large amounts of heat. The heat must be dissipated. It also contributes to a shortened useful life of such light sources.

There have been numerous attempts to utilize low power (<1 W electrical power consumption, typically operating below 100 mW) LEDs coupled to fiber optic light guides as light sources for endoscopy, dentistry, and for remote illumination of objects (as with a flashlight). Most of these prior attempts employ numerous low power LEDs for remote illumination. Multiple LEDs are necessary because the light output from a single, low power LED is very low and there is poor coupling of light emitted by the LED(s) into the optical fiber. An example of several coupling methods appears in U.S. Pat. No. 6,331,156 whereby the inventors place the fiber optic directly in front of either a surface mount or cylindrical LED without the use of additional optical components, coatings or gel. This patent also exemplifies the use of additional optical components in the form of lenses or mirrors in order to collect light generated from a standard, unmodified LED package configuration. US published patent application 2004/0004846 A1 utilizes a lens to couple the light emitted by an LED into a fiber optic. US published patent application 2003/0156430 A1 describes a device that consists of a number of individual LEDs mounted on mirrors, the arrangement of the LEDs and mirrors having a common focal point at the input end of the fiber light guide. U.S. Pat. No. 6,260,994 describes a plurality of LEDs mounted between a spherical or parabolic reflector and a lens, which directs the light emitted by the LEDs into the light guide fiber. In this invention, the LEDs emit light towards the collecting lens and away from the reflector. In U.S. Pat. No. 6,318,887, the LEDs are positioned so as to emit radiation towards a reflector, which then reflects light through a transparent printed circuit board and towards a lens and fiber light guide. In US published patent application 2002/0120181 A1, light emitted by several LEDs is collected along a common optical axis through a series of beam splitting prisms, in at least one embodiment with the use of lenses to couple the light from the LED into the prism, and then into the fiber. In these examples, the LED packages are not modified; multiple, low power LEDs are employed in order to attain a reasonable level of illumination; and in most of these examples, external optical components are employed in order to increase the coupling efficiency between the LEDs and the light guide fiber.

In US published patent application 2003/0231843, numerous low power LEDs are coupled into individual fibers, which are combined together at the distal end of the device to produce intense light for curing dental epoxy. This patent application describes an approach in which the LED package and light guide fiber are modified in order to increase the optical coupling efficiency between the two. In one embodiment, the cladding material from the fiber is removed and the fiber core is placed within the LED epoxy lens. The exterior of the epoxy lens is coated with a low refractive index "clad" that produces total internal reflection of the light emitted by the LED. Some of the light reflected by this LED clad can make its way into the core of the fiber and be transmitted to the distal end of the device. This patent application also includes a description of a taper attached to the external surface of the LED dome lens that couples the light into the fiber. Again, however, additional optical elements (cladding or tapers applied to the LED) are used. Also, the device employs numerous low power LEDs to attain sufficient light output from the device. This type of arrangement would be difficult if not impossible to implement with a high power LED because of the high operating temperature of these LEDs (up to 135 degrees C.). At high temperatures, the epoxy used in typical LED packages will melt or crack due to thermal cycling. In addition, high temperatures will cause the epoxy to discolor, typically becoming yellow. This will impart a yellow cast to the light, thereby lowering its effective color temperature and its desirability as a visual light source. In addition, discoloration will absorb lower wavelengths of light emitted by the LED, particularly those wavelengths in the blue and UV region of the spectrum that are essential for epoxy curing and fluorescence applications.

SUMMARY OF THE INVENTION

Recent advances in light emitting diodes (LEDs) have seen the advent of very high power LEDs, up to 5 W. This invention utilizes a high power white light LED as a light source for medical and industrial endoscopes. The high power, very small size, and high efficiency of these devices makes it possible to design an untethered endoscope; an endoscope without a light guide umbilical connecting the endoscope to an external light source.

The invention entails an endoscope with a battery powered, high power LED incorporated into the endoscope handle. A light guide is closely coupled to the LED, without the need for additional optical components. Accordingly, a large percentage of the light emitted by the LED is coupled directly into the light guide, which transmits this light to the distal end of the endoscope, or any remote location, and illuminate the object under investigation. The light guide is preferably comprised of a bundle of small diameter fibers configured to closely match the size and shape of the light-emitting surface of the LED.

Several innovative designs for coupling a light guide fiber bundle to the LED are described that produce a sufficient amount of light for illuminating the object. These designs do not include auxiliary optics, such as lenses or mirrors, but rely on the small size of the LED's emitting region and the placement of the light guide directly against the light emitting region. The use of an optical index matching material between the LED's emitting region and the light guide can, in some cases, improve the transfer efficiency of light out of the LED chip into the light guide. Because the LED itself is very efficient in converting electrical energy into light, and the described optical interface is very efficient at coupling this light from the LED into the light guide, this new light source can be powered by small batteries that will operate for a considerable length of time without the need for battery replacement or recharging, and without making the endoscope handle cumbersome or unwieldy. The lack of the need for additional optical components simplifies the mechanical design and volume occupied by the light source.

The high light output and high coupling efficiency of the light emitted by the LED into the light guide increases battery lifetime, or permits the use of smaller capacity, and smaller volume, batteries. The invention could use more than one LED in cases in which there is insufficient light from a single LED and there is sufficient room within the housing to add one or more additional LEDs, which would be coupled to the light guide in the manners described herein. Also, other types of LEDs can be coupled to light guides in a similar manner as is described herein, particularly LEDs with different spectral outputs (such as UV, 430 nm, 470 nm, 530 nm, near infrared, infrared, etc.), LEDs produced by other manufacturers (such as Nichia, Microsemi, etc.), and LEDs with different form factors (such as the flat Microsemi OPTO3 package, round or cylindrical LED package (T1, T1¾, etc.), or small surface mount package).

The preferred embodiment of this invention relates specifically to medical and industrial endoscopes, both flexible and rigid. However, this invention also has applications in other areas, such as: fiber optic lighting; delivery of light from other regions of the spectrum, such as the ultraviolet, near infrared, and infrared; and other types of optical observations such as fluorescence, absorbance, and transmittance measurements. Additionally, this light source device can be used as a remote light source (fiber optic flashlight) for visual inspection. This fiber optic and LED light source can also be made explosion proof because of its low voltage, low power consumption, and small volume; details of this would be apparent to those skilled in the art.

BRIEF DESCRIPTION OF THE DRAWINGS

Other objects, features and advantages will occur to those skilled in the art from the following description of the preferred embodiments, and the accompanying drawings, in which:

FIG. 1 is a greatly enlarged partial cross sectional diagram of the preferred embodiment of the high power LED-based light source of the invention;

DETAILED DESCRIPTION OF THE PREFERRED EMBODIMENTS

Figure 1A:
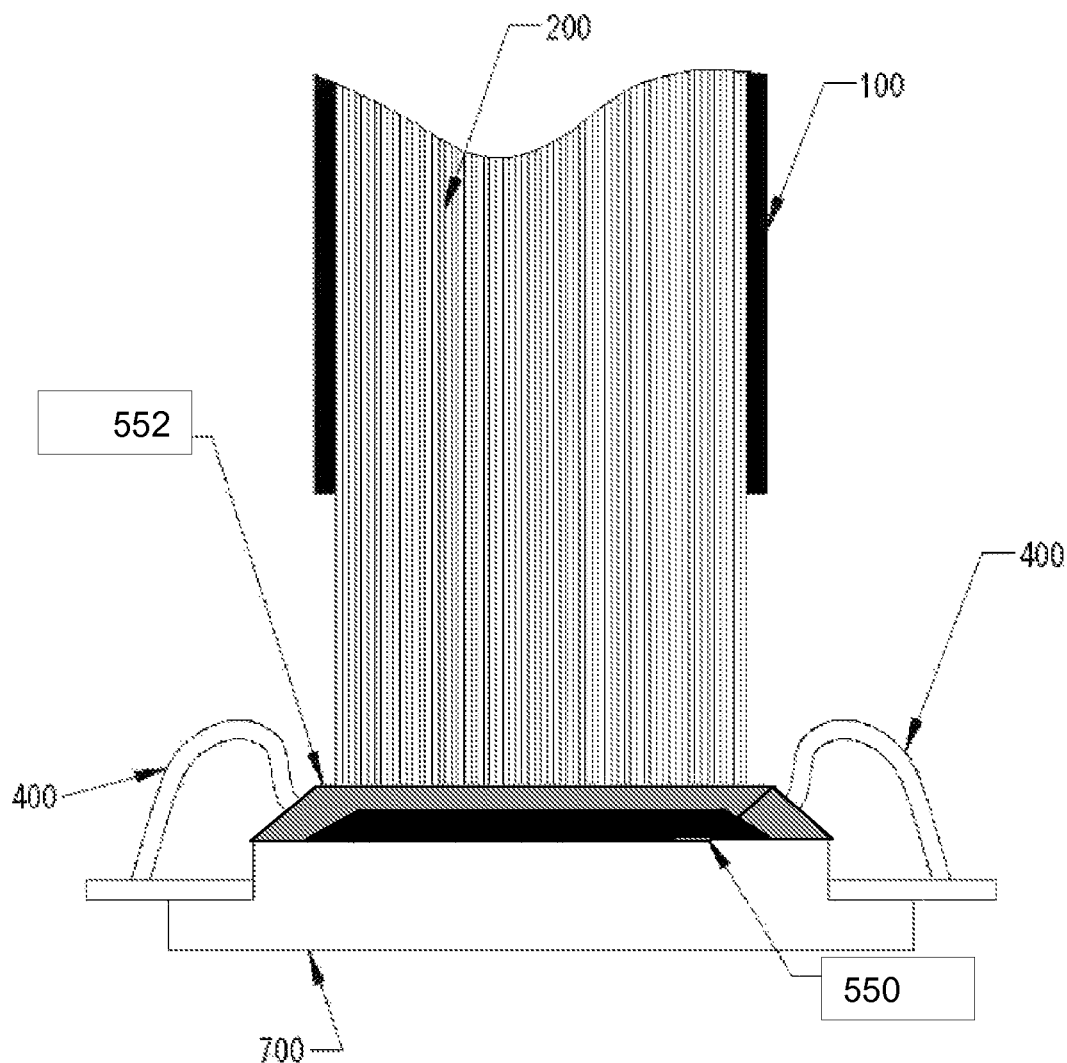
FIGS. 1A and 1B are a greatly enlarged partial cross sectional diagram of a flat package.

The preferred embodiment of this invention utilizes a high power LED (Luxeon III Model LXHL-LW3C, Lumileds Lighting, LLC, 370 W. Trimble Road, San Jose, Calif. 95131) with a typical forward voltage of 3.7V and operating current at 700 mA. This device can be safely operated up to a current of 1 A with a corresponding typical forward voltage of 3.9V. This white LED has a typical color temperature of 5500K. The LED chip has an emitting surface of approximately 1 mm×1 mm, and is coated with a wavelength conversion phosphor (and/or fluorophor) that emits a broadband continuum of visible white light between about 470-700 nm.

The light emitting area of the LED is coupled to a small 1 mm square or round bundle of light guide fibers; a typical light guide bundle size used in endoscopes. The light guide bundle is composed of hundreds of individual glass (or plastic) fibers grouped together to form a single bundle at the light source, and either a single bundle or multiple bundles at the distal end of the endoscope. Such bundles can take on a variety of shapes at the distal end depending upon the design of the particular endoscope: one or more round bundles, a circular halo, a crescent, or the like. Small diameter fibers, typically 30-50 micrometers in diameter, are employed because these small fibers are flexible (necessary for flexible endoscopes that bend during use), or because they are required to fit into the narrow spaces around the optics either in the shaft or distal head of the endoscope.

Other types of light guides can be coupled to the LED in the manners described herein, including: liquid light guides, plastic or glass fibers, plastic or glass rods, and tapers made from fibers (glass and plastic) or solid tapers (glass and plastic). Single glass or plastic fibers may comprise the light guide. Such fibers around 1 mm in diameter are typically flexible. In order to accommodate a small light guide bundle of less than the LED emitting area, a fiber optic or solid plastic or glass taper may be placed between the LED emitting surface and the bundle, acting as an adapter that captures substantially all of the light emitted from the LED and efficiently couples it into the fiber bundle that delivers the light to the distal end of the instrument.

The details of the endoscope or other device in which the light source is used are known to those skilled in the art, for example as disclosed in U.S. Pat. No. 6,260,994 (incorporated herein by reference). This holds true whether the light source is used in a medical or industrial endoscope (either flexible or rigid) or other application areas such as fiber optic lighting, delivery of light from other regions of the spectrum, other types of optical observations such as fluorescence, absorbance, and transmittance measurements, and remote light sources akin to fiber optic flashlights, used primarily for visual inspection.

The high-power white light-emitting LED chip is commercially supplied encapsulated in a silicone optical gel covered by a plastic dome lens assembly, which spreads the emitted light over a 160 degree angle (total included angle at which 90% of the total luminous flux is captured). A considerable amount of light can be captured by placing the light guide at the surface of this dome lens or utilizing additional optical components (lenses, mirrors, tapers, etc.) to couple the light into the fiber bundle. However, a much larger portion of light can be captured by moving the light guide adjacent to the surface of the LED chip.

Figure 1B:
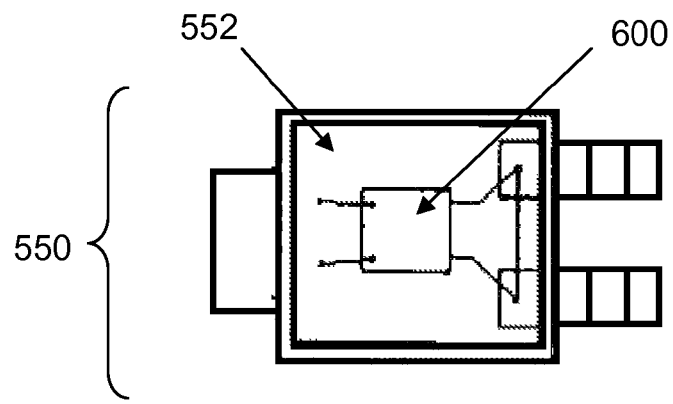

FIG. 1 demonstrates how the maximum coupling of light from the LED chip into the light guide is achieved. The plastic lens and coupling gel as supplied with the LED are first removed, exposing the LED chip 600 and its phosphor coating 500. LED chip 600 is supplied mounted on heat sink 700. Wires 400 supply power to LED chip 600. A bundle of polished light guide fibers 200 having a flat face (typically filling the entire emitting area of chip 600) is epoxied into a stainless steel ferrule 100, which is ideally the same shape and size as the LED chip emitting surface area. Other materials can be used for the construction of the ferrule, such as other metals, alloys, and plastics, or the ferrule can be eliminated altogether when not needed for grouping a large number of fibers together (such as when a single, large diameter fiber or rod is used instead of a group of fibers). The end of ferrule 100 can be coincident with the light guide 200 face, or can be slightly recessed from the face of the polished light guide 200 in order to reduce the size of the end of this light guide. The polished light guide 200 face is placed in contact with the surface of LED chip 600, or as close to this surface as mechanically possible. Ideally, both faces are as flat as possible, which accomplishes actual contact or very minute separation across all or a substantial portion of the interface between the LED surface and the face of the light guide. The flexibility of the light guide fibers can assist in a higher degree of contact between the two faces. This ensures the most efficient coupling of light out of LED chip 600 into light guide 200.

Figure 2:
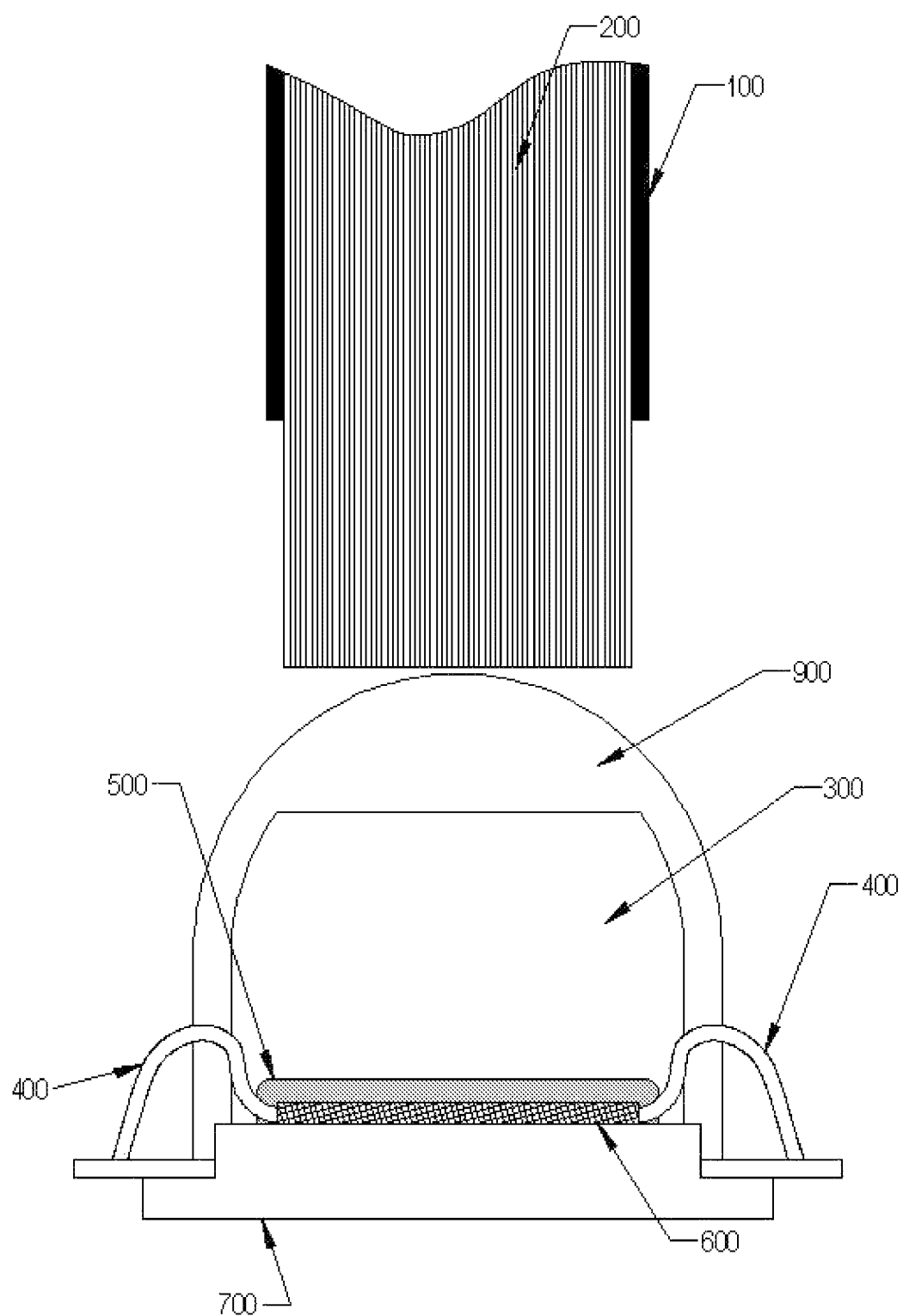
FIG. 2 is a similar diagram for an alternative embodiment of the inventive light source.
Figure 3:
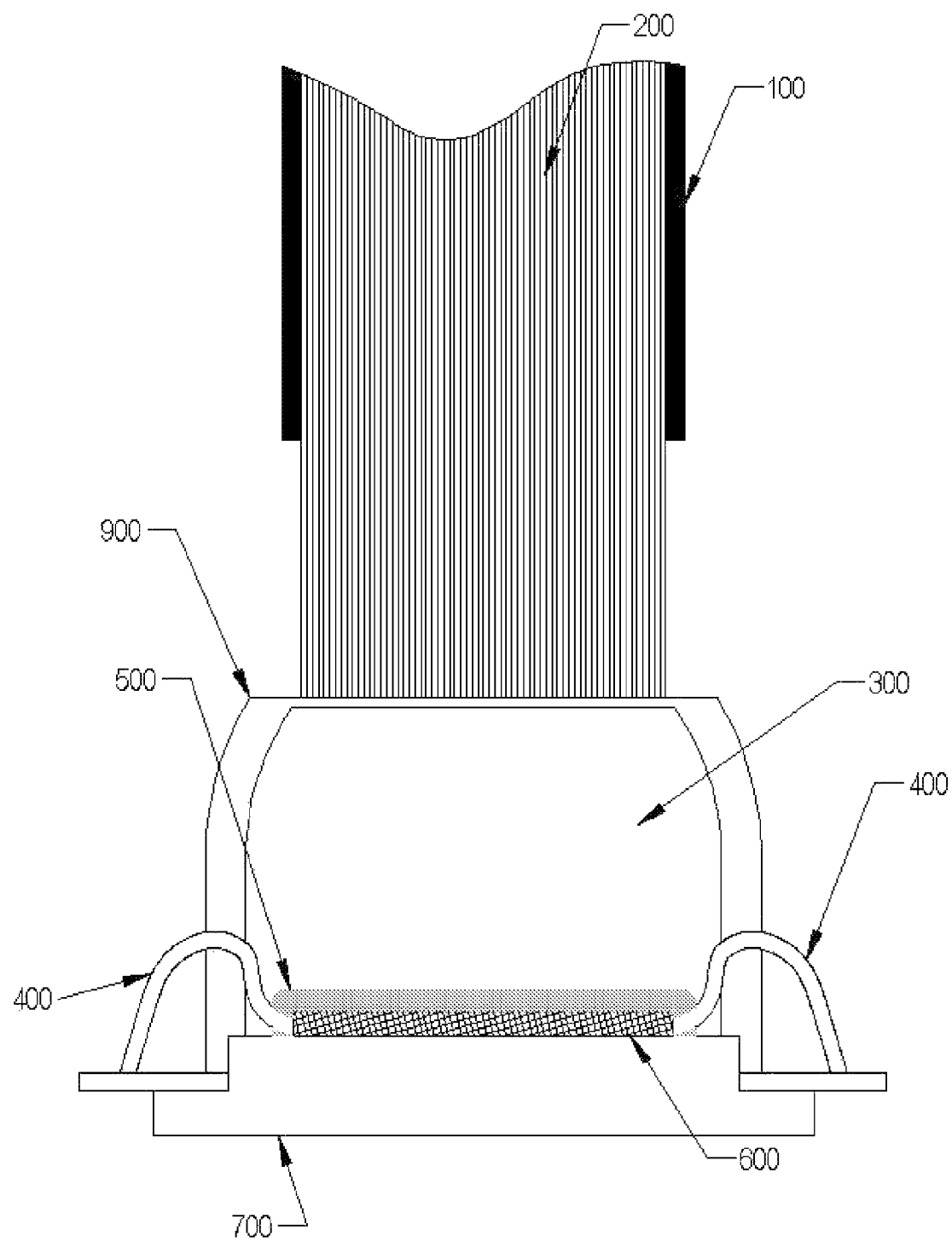
FIG. 3 is a similar diagram of yet another alternative embodiment of the light source of this invention.

Other embodiments of the invention are also anticipated and are now described. FIGS. 2 and 3 demonstrate how the LED can be coupled to a light guide with little or no modification to the LED housing. In FIG. 2, light guide 200 is placed directly adjacent to the LED dome lens 900. Sufficient light may be coupled into light guide 200 to illuminate the object of interest. However, the optical transfer efficiency of this coupling is very poor, resulting in a lower level of illumination of the object as compared to the preferred embodiment described above. This can be compensated at least in part by operating at higher power, which may increase the light output but also lowers battery and LED lifetime.

In FIG. 3, dome lens 900 of the LED is ground and polished nearly down to the level of internal silicone encapsulent 300, so as to preserve the integrity of the mechanical package. This increases the amount of light available to light guide 200, as the amount of light present at any plane above the surface of LED chip 600 is inversely proportional to the distance between this plane and the LED chip. Therefore, if the distance from the LED chip to the light guide's polished face is reduced from 3 mm to 2 mm, an increase in light density (light per unit area) of 2.25 times is achieved. To further improve the amount of light coupled into light guide 200, an index matching material (not shown) can be placed between the LED's dome lens 900 and light guide 200.

Figure 4:
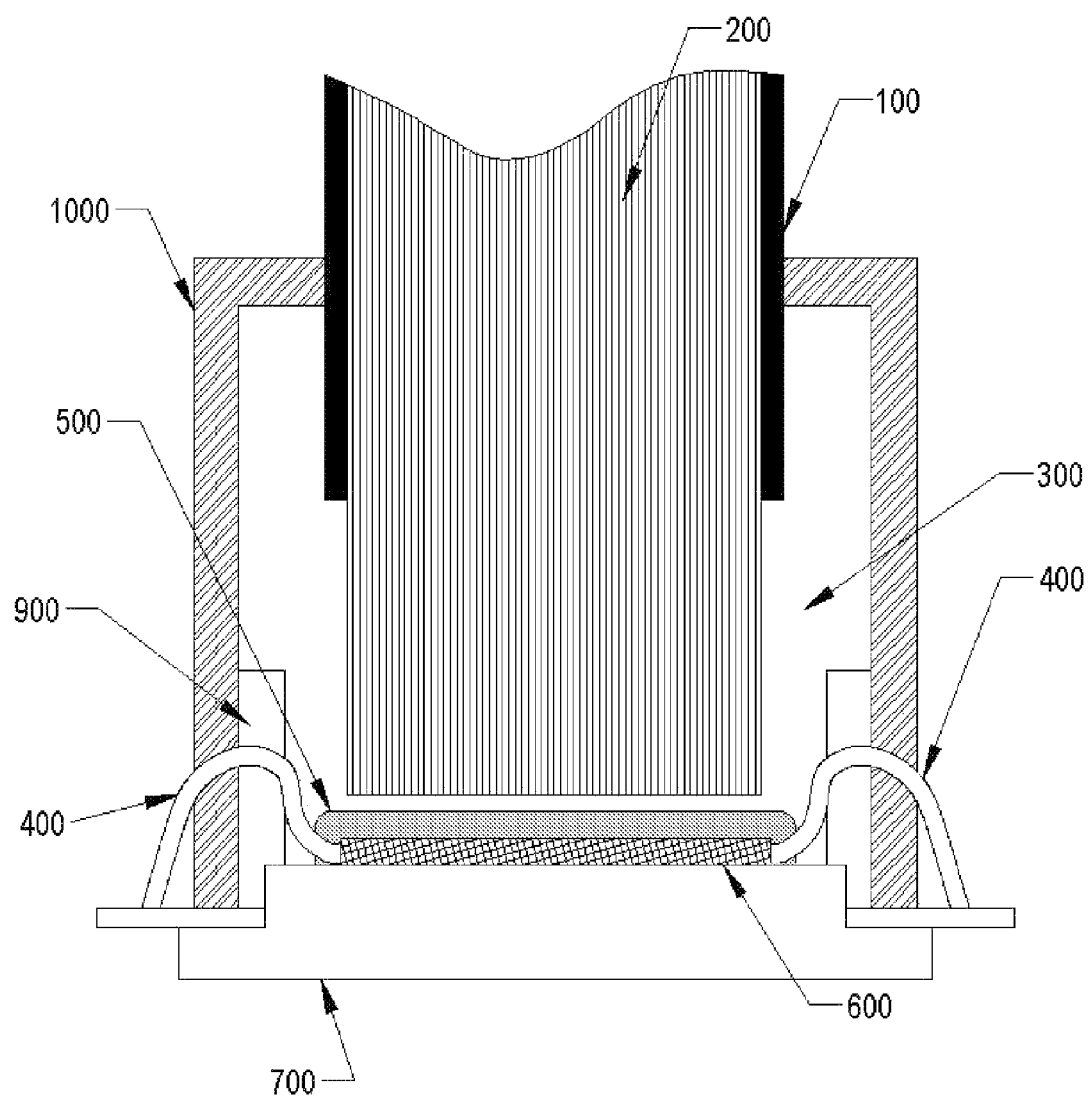
FIG. 4 is a similar view of another embodiment of the inventive light source.

FIG. 4 depicts yet another embodiment of the invention in which LED dome lens 900 is partially removed so as to expose the LED's silicone encapsulent material 300 that encapsulates LED chip 600 and phosphor 500. Light guide 200 can then be immersed in the LED's index matching material 300, and placed in close proximity to the emitting surface of the LED. This can be accomplished without the need to disturb the original index matching material 300, thereby avoiding the possibility of introducing air bubbles within the optical path. Care should be taken so as not to introduce air between light guide 200 and silicone encapsulent 300. This can be accomplished by assembling the components in a vacuum glove box, or by inclining light guide 200 at a slight angle when placing it in silicone encapsulent material 300. As light guide 200 is lowered into silicone encapsulent 300, the fiber is slowly inclined back towards perpendicularity with respect to LED chip 600 without trapping air bubbles at the interface. Sleeve 1000 can then be inserted over ferrule 100 and the LED assembly, and fastened in place either with adhesives or by mechanical means. This will hold light guide 200 in place and prevent silicone encapsulent 300 from flowing out of modified dome lens 900 at a later time. Sleeve 1000 is optional.

In some instances, it is desirable to employ an index matching material between the fiber bundle and the LED chip, or the combination of the LED chip and its phosphor. The index matching material helps to couple the emitted light into the light guide, and typically has an index of refraction between that of the light emitting surface and that of the light guide. The material can be a gel. Examples of when an index matching material is desirable are: when the emitting surface is a substrate that the LED chip is mounted to, such as sapphire (n=1.76, where "n" is the refractive index), or when the LED chip is the emitting surface and it possesses a high refractive index. Examples of LED chips with very high refractive indices include chips manufactured from gallium nitride (n=2.5), gallium phosphide (n=3.31), and gallium arsenide (n=4.02). The amount of light coupled into the light guide from the LED can be increased, potentially by up to a factor of two, when an appropriate index matching material is employed between the LED and the fiber. The index matching material may also substitute for the silicone encapsulent 300; the silicone encapsulent 300 being a specific type of index matching material.

While the preferred embodiment of this invention utilizes a Luxeon III LED with a 1 mm square emitting surface, other LED package designs also lend themselves to the inventive technique of capturing light by a light guide, which may be accomplished with a fiber bundle. Some examples of these other package designs include the industry standard T1 (3 mm) and T1¾ (5 mm) packages in which the LED chip is enclosed in an epoxy dome lens. It is readily apparent to those skilled in the art to understand how the epoxy package can be removed down to the level of the LED chip and coupled to the light guide. Similarly, the flat package 550 design shown in FIGS. 1A and 1B, of the Microsemi (Microsemi Corporation, 580 Pleasant Street, Watertown, Mass. 02472) UPW3LEDxx, readily lends itself to fiber coupling by directly bonding the light guide fiber 200 to the face of the window 552 adjacent to the LED chip 600, with or without an index matching material between the window 552 and the fiber 200 as is described in FIG. 4, substituting an index matching gel for the silicone encapsulent.

Other embodiments will occur to those skilled in the art and are within the following claims.

What is claimed is:
1. An illumination device comprising:
a high-power solid state light-emitting device having a flat package, the flat package comprising a structural window material encasing a light-emitting element of the light-emitting device on exposed top and side surfaces of the light emitting element such that the structural window material is disposed adjacent to and in contact with a light-emitting surface of the light-emitting element and has a flat face opposite the light-emitting surface, wherein the flat face directly light couples to a light guide; and the light guide comprising a light-receiving end and a light-transmitting end, wherein the light-receiving end is in contact with proximate to the face of the structural window material;

wherein the structural window material comprises a ground dome lens having a flat top surface.

2. The illumination device according to claim 1, wherein the light-receiving end of the light guide matches a size and shape of the light-emitting surface of the light-emitting device semiconductor chip.

3. The illumination device according to claim 1, wherein the light-receiving end of the light guide is substantially flat.

4. The illumination device according to claim 1, wherein the light-emitting element further comprises a wavelength-conversion phosphor.

5. The illumination device according to claim 4, wherein the wavelength-conversion phosphor is disposed between the light guide and the light-emitting surface.

6. The illumination device according to claim 4, wherein the light-emitting surface of the light-emitting element is coated with the wavelength-conversion phosphor.

7. The illumination device according to claim 1, wherein the light guide comprises a bundle of optic fibers.

8. The illumination device according to clause 1, wherein the light guide comprises a single glass or plastic fiber.

9. The illumination device according to claim 1, wherein the light-receiving end is directly bonded to the flat face of the flat package.

10. The illumination device according to claim 9, wherein the light-receiving end of the light guide matches a size and shape of the light-emitting surface of the light-emitting device semiconductor chip.

11. The illumination device according to claim 1, wherein an index matching material is disposed between the structural window material of the flat package and the light-receiving end of the light guide.

12. The illumination device according to claim 1, wherein the window comprises a solid face.

13. The illumination device according to claim 1 wherein the light-emitting device is mounted on and in contact with a heat sink material.

14. An illumination device comprising:
a high-powered solid state light-emitting device having a package, the package comprising a light-emitting element and a flat structural window material, wherein the light-emitting element defines a light-emitting surface and the flat structural window material is adjacent to and in contact with the light-emitting surface, wherein the structural window material encases the light-emitting element on exposed top and side surfaces is encased within the package such that the structural window material has a flat surface that directly light couples to a light guide; and the light guide comprising a flat light-receiving end and a light-transmitting end, wherein the flat light-receiving end is in contact with proximate to the flat structural window material;

wherein the structural window material comprises a ground dome lens having a flat top surface.

15. The illumination device according to claim 14, wherein the light-emitting element further comprises a wavelength-conversion phosphor.

16. The illumination device according to claim 15, wherein the light-emitting surface of the light-emitting element is coated with the wavelength-conversion phosphor.

17. The illumination device according to claim 15, wherein the wavelength-conversion phosphor is disposed between the light guide and the light-emitting surface.

18. The illumination device according to claim 14, wherein the light guide comprises a bundle of optic fibers.

19. The illumination device according to claim 14, wherein the light guide comprises a single glass or plastic fiber.

20. The illumination device according to claim 14, further comprising a battery power source for the light-emitting device.

21. The illumination device according to claim 14, wherein the flat light-receiving end is directly bonded to the flat window.

22. The illumination device according to claim 14, wherein an index matching material is disposed between a window of the flat package and the light receiving end of the light guide.

23. The illumination device according to claim 14 wherein the light-emitting device is mounted on and in contact with a heat sink material.

* * * * *